US009382176B2

(12) United States Patent
Grandbois et al.

(10) Patent No.: US 9,382,176 B2
(45) Date of Patent: Jul. 5, 2016

(54) PROCESS FOR THE PRODUCTION OF CHLORINATED PROPENES (71) Applicant: BLUE CUBE IP LLC, Midland, MI (US)

(72) Inventors: Matthew L. Grandbois, Midland, MI (US); Brian Murdoch, Midland, MI (US); Matthew M. Meyer, Canton, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/770,860

(22) PCT Filed: Feb. 27, 2014

(86) PCT No.: PCT/US2014/018826
§ 371 (c)(1),
(2) Date: Aug. 27, 2015

(87) PCT Pub. No.: WO2014/134233
PCT Pub. Date: Sep. 4, 2014

(65) Prior Publication Data
US 2016/0009615 A1 Jan. 14, 2016

Related U.S. Application Data (60) Provisional application No. 61/769,908, filed on Feb. 27, 2013.

(51) Int. Cl.
*C07C 17/26* (2006.01)
*C07C 17/269* (2006.01)
*C07C 17/278* (2006.01)
*C07C 17/358* (2006.01)
*C07C 17/25* (2006.01)

(52) U.S. Cl.
CPC .............. *C07C 17/269* (2013.01); *C07C 17/25* (2013.01); *C07C 17/278* (2013.01); *C07C 17/358* (2013.01); *C07C 2101/02* (2013.01); *Y02P 20/582* (2015.11)

(58) Field of Classification Search
CPC .... C07C 17/25; C07C 17/269; C07C 17/178; C07C 23/04; C07C 2101/02
USPC ......................................................... 570/237
See application file for complete search history.

(56) References Cited

U.S. PATENT DOCUMENTS

| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |

(Continued)

FOREIGN PATENT DOCUMENTS

| CH | 609022 | 6/1974 |
| CN | 101215220 | 7/2008 |

(Continued)

OTHER PUBLICATIONS

Bai, et al., "Isomerization of Tetrachloropropene to Promote Utilization Ratio of Triallate Raw Materials", Petrochemical Technology & Application, 2007, 25(1).
Chai, et al., "Study of Preparation of 1,1,1,3-tetrachloropropane", Zhejiang Chemical Industry, 2010, pp. 1-3, 41(5).
Cristiano, et al., "Tetraalkylphosphonium Trihalides. Room Temperature Ionic Liquids as Halogenation Reagents", J. Org. Chem., 2009, pp. 9027-9033, 74.
Evstigneev, et al., "Initiated Chlorination of Tetrachloropropane", Khim. Prom., 1984, pp. 393-394, 16(7).

(Continued)

*Primary Examiner* — Jafar Parsa
(74) *Attorney, Agent, or Firm* — Polsinelli PC (57) ABSTRACT

Processes for the production of chlorinated propenes are provided. The processes proceed through the production of cyclic intermediate that is thereafter readily converted to a desired chloropropane, e.g., via selective pyrolysis. The process may be conducted using starting materials that are readily commercially available and/or that may be reacted safely in standard laboratory equipment so that capital cost savings may be seen. The process does not require the use of catalysts and yet, process conditions less extreme than many conventional processes for the production of chlorinated propenes are suitable, so that raw material and utility cost savings are also possible.

13 Claims, 2 Drawing Sheets

(56) References Cited

U.S. PATENT DOCUMENTS

| | | |
|---|---|---|
| 3,920,757 A | 11/1975 | Watson |
| 3,926,758 A | 12/1975 | Smith |
| 3,948,858 A | 4/1976 | Wiersum |
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Mueller et al. |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo |
| 8,581,012 B2 | 11/2013 | Tirtowidjojo |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,907,149 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2005/0245774 A1 | 11/2005 | Mukhopadhyay et al. |
| 2006/0150445 A1 | 7/2006 | Redding |
| 2006/0258891 A1 | 11/2006 | Mukhopadhyay |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0088547 A1 | 4/2009 | Schamshurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2009/0253946 A1 | 10/2009 | Van Der Puy |
| 2009/0270568 A1 | 10/2009 | Strebelle et al. |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0155942 A1 | 6/2011 | Pigamo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |

(56) References Cited

U.S. PATENT DOCUMENTS

| | | |
|---|---|---|
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| CN | 103562164 A | 2/2014 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0131560 | 1/1985 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2007-535561 | 5/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39 (5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.l. The Peroxide-Catalyzed Chlorination of Hydrocarbons", JACS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Choloorination of Chloroolefins C3-C4", Doklady Chemistry, vol. 386, No. 4, 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry, Feb. 1, 1941, pp. 176-181, 33(2).

Michigan Technological Univ., "Free-Radical Chlorination with Sulfuryl Chloride", Nov. 15, 2001, 1-7.

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)Cl Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

(56) References Cited

OTHER PUBLICATIONS

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, WI-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

Tanuma, et al., "Partially Fluorinated Metal Oxide Catalysts for a Friedel-Crafts-type Reaction of Dichlorofluoromethane with Tetrafluoroethylene", Catal. Lett., 2010, pp. 77-82, 136.

Tobey, et al., "Pentachlorocyclopropane", Journal of the American Chemical Society, Jun. 1, 1996, pp. 2478-2481, 88 (11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the suboptimal processes typically utilized in their manufacture. Conventional processes for the manufacture of chlorinated propenes may typically involve multiple chlorination procedures on less substituted propane precursors, which may require the use of extreme operating conditions and/or expensive catalysts or reagents. Even if such conditions, catalysts and/or reagents are utilized, many conventional processes for the production of chlorinated propenes may yet suffer from low selectivity and/or low yield. Any of these alone, much less all of them combined, can render the conventional production of chlorinated propenes prohibitively expensive on the large scale required to be useful as feedstocks for the production of downstream products.

It would thus be desirable to provide improved processes for the production of chlorocarbon precursors useful as feedstocks in the synthesis of refrigerants and other commercial products. More particularly, such processes would provide an improvement over the current state of the art if they were less costly in starting materials, while yet providing higher selectivity and/or yield.

BRIEF DESCRIPTION

The present invention provides such processes. More particularly, the present processes are capable of continuous operation and produce a cyclic intermediate that is thereafter readily converted to a desired chloropropane, e.g., via selective pyrolysis. The process may be carried out in either the gas or liquid phase, and results in the formation of only trace amounts of impurities. As a result, product separation/purification is simplified. The process requires conditions less extreme than many conventional processes for the production of chlorinated propenes, so that utility cost savings are possible. Exotic materials are not required, and indeed, the process may be conducted using starting materials that are readily available and/or that may be reacted safely in standard laboratory equipment so that capital cost savings may be seen. Indeed, the process does not require the use of catalysts, and raw material savings may also be realized.

In a first aspect, a process for the production of chlorinated propenes is provided. The process operates continuously, and results in the production of a cyclic intermediate that is thereafter converted to the desired chlorinated propene. The cyclic intermediate may be a cyclopropane, and in some embodiments, may comprise 1,1,2,2-tetrachlorocyclopropane. The cyclopropane is prepared from reactants comprising a geminally chlorinated alkene and a carbene.

In some embodiments, the geminally chlorinated alkene comprises vinylidene chloride, perchloroethylene, trichloroethylene, 1,1-dichloropropene, 1,1,2-trichloropropene, or a combination of these. The carbene may be, e.g., methylene, dichlorocarbene, dibromocarbene, chlorobromocarbene, or a combination of these and in some embodiments, may be generated in situ, e.g., using sodium trichloroacetate, diazomethane, chloroform. In embodiments wherein chloroform is used, the process advantageously does not require the use of caustic to produce the reactive dichlorocarbene.

The process may be conducted in either the gas or liquid phase, or both. In some embodiments, the reactants may be provided in the liquid phase and then preheated or vaporized, prior to being brought into contact with each other. In those embodiments of the process wherein chloroform is used as a reactant, for example, the chloroform may desirably be preheated to a temperature of greater than 200° C., or to a temperature of from 250° C. to 400° C., or from 250° C. to 350° C. In those embodiments of the process wherein vinylidene chloride is used as a reactant, for example, the vinylidene chloride may be preheated to a temperature of greater than 30° C., or to a temperature of from 50° C. to 200° C., or from 50° C. to 100° C. At such temperatures, chloroform and vinylidene chloride, respectively, are expected to vaporize and may be introduced into an appropriate reactor so that the process proceeds in the gas phase.

Whatever the reactor, it may advantageously be operated at conditions appropriate for a gas phase reaction between the chosen reactants. For example, in some embodiments, the vaporized reactants may be passed through a hot tube reactor. For those embodiments wherein the reactants comprise chloroform and vinylidene chloride, a hot tube reactor may be operated at temperatures greater than 250° C., or greater than 350° C., of from 400° C. to 600° C. In such embodiments, the chloroform and vinylidene chloride are desirably brought into contact prior to being heated to temperatures above 400° C.

Appropriate operating pressures for a hot tube reactor used in the present process may generally be less than 20 psig, or from 0 to 10 psig, or from 0 to 5 psig. A carrier gas may be used, if desired, to assist the progress of the reactants/products/byproducts through the reactor, and in such embodiments, nitrogen and/or any other inert gas may be used. The desired chloropropene may be produced after only one pass through a hot tube reactor operated under such conditions.

Appropriate separation techniques may be applied to recover the desired product and unreacted reactants, e.g., chloroform, vinylidene chloride, and/or the cyclopropane intermediate, may either be recycled or disposed of. In some embodiments, the desired chlorinated propene may comprise from 3 to 5 chlorine atoms.

The process may also be conducted in the liquid phase and if the same is desired, a cyclic intermediate, e.g., cyclopropane, may be prepared from reactants comprising sodium trichloroacetate and vinylidene chloride, or diazomethane and perchloroethylene.

Due to the simplicity of the process, and ready commercial availability of suitable reactants and economical prices, the present process is advantageously used to produce chlorocarbon precursors useful as feedstocks in the synthesis of refrigerants and other commercial downstream products such as, e.g., 2,3,3,3-tetrafluoroprop-1-ene or 1,3,3,3-tetrafluoroprop-1-ene. The advantages provided in the present process are thus expected to carry forward into processes for the production of such refrigerants, and the same is contemplated.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

As used herein, the term "yield" means the amount of a specific chemical species present within the post-pyrolysis stream as a percentage of the total amount of material present, and the term "selectivity" means the combined yields of desired products and intermediates that would ultimately give the desired tetrachloropropene intermediate corrected for recovered starting material.

The present invention provides efficient processes for the production of chlorinated propenes via the production of a cyclic intermediate that readily converts to the desired chlorinated propene. Although facile conversion of cyclic intermediates to provide chlorinated propenes has been explored in the art, the processes in which it has been employed have been relegated to batch-wise operation, and even then, under extreme conditions, i.e., of high temperatures (temperatures of 500° C. or greater) or pressures (greater than 50 psig), and/or using exotic and/or expensive reactants. In contrast, the present processes make use of readily available and economical reactants, and utilizes mild reaction conditions, i.e., temperatures of less than 500° C., and pressures of less than 50 psig. Catalysts or initiators are not required, although they may be employed in some embodiments, if desired.

Due at least in part to the use of mild reaction conditions, the present processes, whether conducted in the gas or liquid phase, and in the presence or absence of optional initiators, result in the formation of only trace amounts of impurities. And so, whereas conventional processes for the production of chlorinated propenes via production of a cyclic intermediate may exhibit selectivities of 30% or less to the desired product, the present processes exhibit selectivities to the desired chlorinated propene of greater than 50%, or greater than 70%, or greater than 80%, or even greater than 84%, based upon the amount of cyclic intermediate formed.

In other words, in conventional processes wherein much higher temperatures, pressures and/or catalysts are utilized, the rates of all reactions taking place in the process are affected, including side reactions, so that higher concentrations of byproducts are formed and selectivity to the desired product can thus be reduced. For example, one conventional approach for providing, e.g., 1,1,2,3-tetrachloropropene, involves the formation of a cyclic intermediate followed by pyrolysis of the same at temperatures of 500° C. or greater. Although the selectivity of this high temperature conventional process is 82.5%, yield to the desired chloropropene is only 27.8%.

In contrast, in the present process, milder reaction conditions, and in some embodiments, no catalysts, are utilized. As a result, while lower conversions may result, once the cyclic intermediate is formed, extremely high conversions to the desired chlorinated propene may be seen. Indeed, most, if not all, byproducts formed in the present process are formed in connection with the in situ formation of the carbene provided for in some embodiments. Thus, while selectivities of the present process can range from 50% to 84%, yields to the desired chloropropene of at least 30% are seen.

The present processes also make use of less exotic reactants than conventional processes for producing chlorinated propenes via a cyclic intermediate. For example, one conventional process for the formation of 1,1,2,3-tetrachloropropene via formation of a cyclic intermediate calls for the reaction of chlorofluorosilane compound, or brominated mercury with an alkene. In contrast, the present process may be conducted with a geminally chlorinated alkene and a carbene.

In some embodiments, the geminally chlorinated alkene may be one in which both carbon atoms connected by a double bond are geminally chlorinated, although this is not required. Suitable geminally chlorinated alkenes thus include, but are not limited to, vinylidene chloride, perchloroethylene, trichloroethylene, 1,1,-dichloropropene, and 1,1,2-trichloropropene.

Suitable carbenes include, for example, methylene, dichlorocarbene, dibromocarbene, and chlorobromocarbene. While any of these, or combinations of these are suitable, dichlorocarbene offers the advantage of also being geminally chlorinated, while methylene, dichlorocarbene and dibromocarbene also offer the capability of being produced in situ—methylene via the thermal degradation of diazomethane and dichlorocarbene or dibromocarbene via the thermolysis of chloroform or tribromomethane, respectively. Precursors to either the geminally chlorinated alkene or carbene, and in particular those capable of undergoing in situ conversion to either, are thus also suitable for use in the process, and contemplated to be within its scope.

Catalysts are not required in the present process. Indeed, although many conventional processes for the production of chlorinated propenes through a cyclic intermediate assert that the process occurs via a free radical mechanism, and thus, require the use of free radical initiators, it has now been surprisingly discovered that free radical catalysts in fact, have no, or very little, impact on the present process. In order to confirm this surprising result, free radical inhibitors were added to the present process, and resulted in no discernible inhibition of the process. Since the present process was thus confirmed as proceeding via a mechanism other than via a free radical process, free radical initiators have no effect on the reaction rate, and are not necessary in the present process. Exclusion of the same is thus contemplated, and cost savings thus provided.

In some embodiments, one or both the geminally chlorinated alkene and carbene are advantageously preheated in order to vaporize them and/or increase their respective reactivity within the cyclopropane forming reaction. In some embodiments, e.g., wherein the carbene is desirably formed in situ as may be done in the case of methylene and dichlorocarbene, preheating at least the carbene forming reactant can assist in its formation. For example, in those embodiments wherein one reactant comprises chloroform, preheating the same can result in its thermal degradation to provide dichlorocarbene. Although some conventional methods for forming dichlorocarbene from chloroform call for the use of caustic to assist in this reaction, caustic is not required in the present process, and elimination of the same can result in additional cost savings.

In other embodiments, either or both the geminally chlorinated alkene and/or carbene may be provided in the liquid phase. And, embodiments are contemplated wherein one reactant is desirable vaporized, if only to provide for the in situ formation of the reactant, while the other remains in the liquid phase. In such embodiments, one or more phase transfer catalysts may desirably be utilized in order to assist in the reaction of the two phases. Those of ordinary skill in the art are familiar with such catalysts and any useful for this purpose may be used. Suitable nonlimiting examples include quaternary ammonium and quaternary phosphonium salts.

If some or all of the process is desirably carried out in the liquid phase, solvents may be used, if desired. Desirably, if a solvent is utilized, it will increase the accessibility of the reactants to each other, while not interfering with the reaction thereof. Those of ordinary skill in the art are capable of determining suitable solvents based upon the chosen reactants and reaction conditions without undue experimentation. Suitable nonlimiting examples include methanol, dimethylethyl ether, bis-dimethylethyl ether, tetrahydrofuran, chloroform, water, acetone, or combinations of these.

The processes may be conducted in any suitable reactor, and advantageously may be carried out in a simple reactor, such as a simple hot tube reactor. In some embodiments, packing may be provided to increase the surface area, and thus assist with heat transfer, within the reactor, if desired.

Particular conditions within the reactor will depend to some extent on the particular reactants chosen and the chlorinated propene desirably produced, and those of ordinary skill in the art are capable of determining the same. Generally speaking, the temperature within the reactor is desirably kept below. e.g., 500° C., to minimize the formation of byproducts and so that selectivities of greater than 50% to the desired chlorinated propene can be seen. Excessive pressure is not required, and indeed, ambient pressure is preferred. If a pressurized environment is desired, e.g., to assist in the control of feed of the reactants, suitable pressures are desirably less than 50 psig. Because mild conditions are utilized, specialized reactors, and or reactor modifications, e.g., jackets and high pressure lines, valves, pumps, etc., are not required.

Once the cyclic intermediate is formed, pyrolysis to the desired chlorinated propene happens quickly at the described conditions and residence time within the reactor is not long. Suitable residence times for the reactants can range from milliseconds to seconds. Flow of the reactants may be assisted through the reactor, if desired or required, by provision of a carrier gas, e.g., nitrogen, or any other inert gas.

As the reactants, byproducts and desired products move through the reactor, they are expected to cool and condense so that the product stream from the reactor is substantially liquid. Nonetheless, active cooling may also be provided, if desired, in order to reduce the temperature of the product stream, e.g., to the lowest condensation temperature of the species in the product stream. For example in those embodiments of the present invention wherein vinylidene chloride is used as the geminally chlorinated alkene, it would be expected to have the lowest condensation temperature of the species present in the product stream at 35° C. and active cooling to provide the entirety of the product stream with this temperature may be used, and may be provided by any suitable cooling apparatus.

One or more separation techniques may then be applied to the product stream to isolate and/or purify the desired product, and in some embodiments, unreacted reactants which may then be recycled to the process, or provided to a downstream process for use as raw material therein. Multiple simple distillations could be performed, i.e., multiple 5 to 10 stage distillation columns could be used until the desired purity/dewatering is seen, or, fewer more complex, separation techniques, e.g., divided wall columns, could be employed. Once presented with the composition of the product stream, those of ordinary skill in the art are capable of determining the appropriate type and number of separation techniques to provide the product, and re-usable unreacted reactants, as well as the parameters for each, without undue experimentation The present processes advantageously can proceed continuously. In contrast, conventional processes for the production of chlorinated propenes via a cyclic intermediate are conducted in a batch-wise fashion, which can result in extended and/or unnecessary exposure of the products to the extreme conditions and even further reductions in selectivity, not to mention the safety concerns that can be raised when attempting to collect the heated, potentially pressurized, products of a reaction involving halogens and/or mercury. In those embodiments wherein the present processes are conducted in a batchwise fashion, as is contemplated, safety issues are minimized and product recovery can be less complex due to the relatively less exotic reactants than e.g., halogenated silanes and/or mercury, used in conventional batch wise processes.

Figure 1:
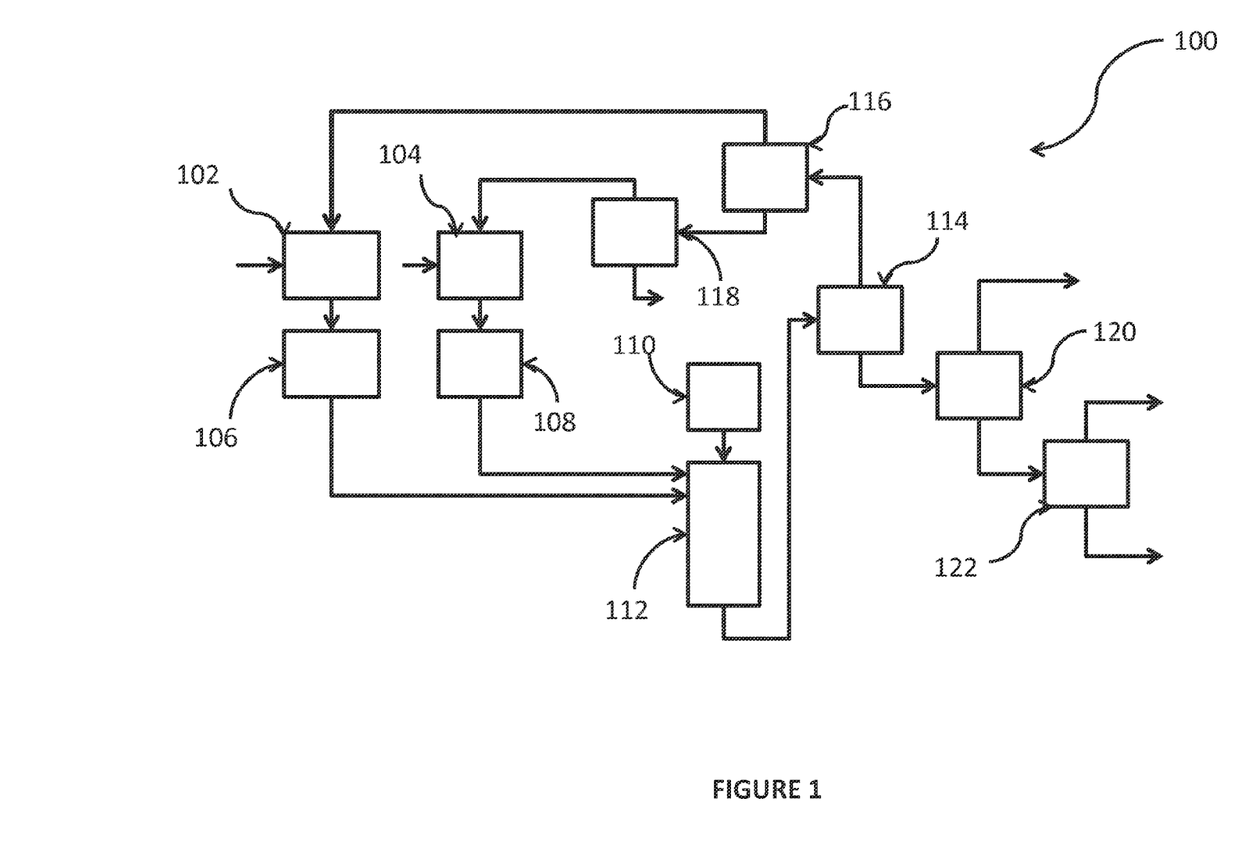
FIG. 1 shows a schematic representation of a process according to one embodiment.

A schematic illustration of one embodiment of such a process is shown in FIG. 1. As shown in FIG. 1, process 100 incorporates holding tanks 102 and 104, preheaters 106 and 108, carrier gas source 110, reactor 112, and separation units 114, 116, 118, 120 and 122.

In operation, the desired reactants would be fed from sources 102 and 104 to preheaters 106 and 108, respectively, wherein they are preheated, and desirably vaporized. In the exemplary embodiment wherein vinylidene dichloride and chloroform are used as reactants, vinylidene chloride may be fed from holding tank 102 to preheater 106 and heated to a temperature greater than 30° C., or to a temperature of from 50° C. to 200° C., or from 50° C. to 100° C. Chloroform may be fed from holding tank 104 to preheater 108 and heated to a temperature of greater than 200° C., or to a temperature of from 250° C. to 400° C., or from 250° C. to 350° C.

Once preheated and/or vaporized, the reactants are provided to reactor 112, which may be, e.g., a hot tube reactor. Movement of the reactants through reactor 112 may be assisted via the provision of a carrier gas, such as, e.g., nitrogen and/or any other inert gas from carrier gas source 110. In some examples it may not be necessary or deemed economically advantaged to use an inert carrier gas.

Reactor 112 may be operated at any suitable conditions, which may appropriately be chosen based upon the reactants and desired chlorinated propene being produced. Advantageously, the conditions utilized need not be extreme—i.e., excessive temperatures and pressures are not required.

For example, for the embodiment wherein chloroform and vinylidene chloride are reacted to provide, e.g., 1,1,2,3-tetrachloropropene via the cyclic intermediate 1,1,2,2-tetracyclopropane, reactor 112 may be operated at temperatures greater than 250° C., or greater than 350° C. In some such embodiments, reactor 112 may be operated at temperatures of from 250° C. to 600° C., or from 400° C. to 550° C. Pressures less than 20 psig are suitable, as is ambient pressure. In some embodiments, reactor 112 may be operated at pressures of from 0 psig to 10 psig, or from 0 psig to 5 psig.

At such reactor conditions, chloroform is expected to decompose to form dichlorocarbene which is further expected to react quickly with the vaporized vinylidene chloride to form the cyclic intermediate—in this case 1,1,2,2-tetrachlorocyclopropane. The cyclic intermediate, in turn, undergoes selective pyrolysis to form 1,1,2,3-tetrachloropropene.

As the reactants, intermediates, products and byproducts progress through reactor 112, they are expected to undergo cooling and condense, so that the product stream from reactor 112 is liquid. Active cooling at the outlet of reactor 112 may also be provided, e.g., via an external heat exchanger (not shown). In such embodiments, the product stream from reactor 112 would also be expected to comprise some amount of chloroform, some 1,1,2,2-tetrachlorocyclopropane, some 1,1,2,3-tetrachloropropene and light and heavy byproducts from the degradation of chloroform, such as methylene chloride, perchloroethylene, 1,1,2,2-tetrachloropropane, pentachloroethane, hexachloroethane, 1,1,2,4,4-pentachloro-1,3-butadiene, and hexachlorobenzene.

This product stream is fed to separation unit 114, which may be operated at conditions effective to provide vinylidene dichloride, chloroform, methylene chloride and other light byproducts in a top stream that is provided to separation unit 116.

Separation unit 116 is operated at conditions effective to provide unreacted vinylidene chloride and lighter byproducts in a top stream, which may be recycled to reactant source 102, or transported to a downstream use or storage. The bottoms stream of separation unit 116, expected to comprise unreacted chloroform and heavier byproducts is provided to separation unit 118, operated at conditions effective to provide substantially pure unreacted chloroform through a top stream that may be recycled to reactant source 104, or provided to a downstream use or storage. The bottoms stream from separation unit 118, expected to comprise byproducts heavier than chloroform, for example carbon tetrachloride or 1,1,2,2-tetrachloropropane may be appropriately disposed of.

The bottom stream from separation unit 114, expected to comprise tetrachloropropene, any cyclic intermediate that did not decompose and heavier byproducts is fed to separation unit 120.

Separation unit 120 is operated at conditions effective to provide a top stream comprising the (any) cyclic intermediate that may be disposed of as waste, or recycled to reactor 112, and a bottoms stream comprising 1,1,2,3-tetrachloropropene and heavier by products. The bottoms stream from separation unit 120 is provided to separation unit 122, which would then provide a substantially pure stream of 1,1,2,3-tetrachloropropene in an overhead stream and the heavier byproducts out a waste bottoms stream.

Process 100 shows multiple separations using simple separation units, e.g., having from 5 to 10 plates. In other embodiments, it may be possible to combine separation units 116 and 118 into one separation unit, as well as separation units 114, 120 and 122. More particularly, it may be possible to replace separation units 116 and 118 and separation units 114, 120 and 122 with one separation unit having more numerous plates, or a divided wall column. Although doing so would require more complex separations to be carried out in a single unit, and perhaps require more sophisticated separation units and/or capital expenditure, time and utility costs may be provided by doing so.

Figure 2:
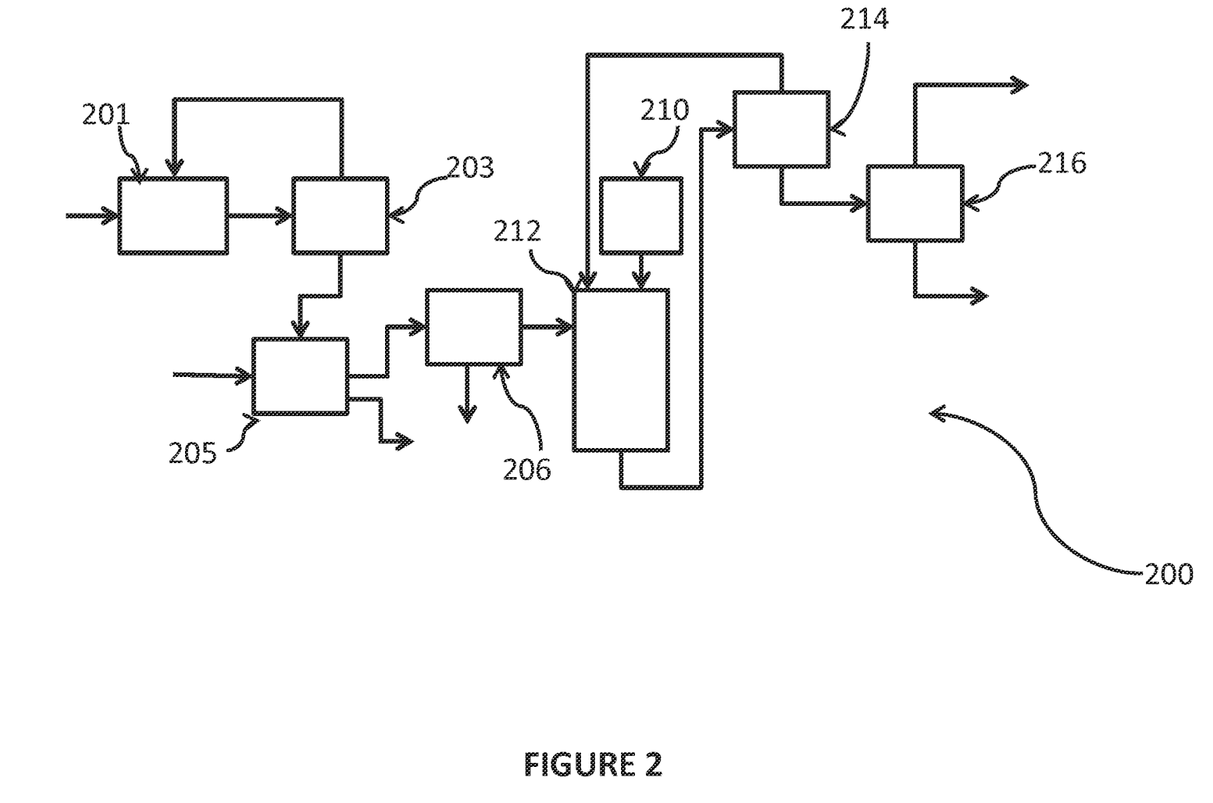
FIG. 2 shows a schematic representation of a process according to a further embodiment.

A schematic illustration of an additional embodiment of the process is shown in FIG. 2. As shown in FIG. 2, process 200 incorporates reactor 201, quench unit 205, preheater 206, reactor 212, carrier gas source 210, and separation units 203, 214 and 216.

In operation, the desired reactants would fed be to reactor 201, operated at conditions to generate the cyclic intermediate therefrom. For example, in those embodiments wherein the reactants comprise, e.g., sodium triacetate and vinylidene dichloride, the same would be provided to reactor 201, optionally along with a solvent and/or a phase transfer catalyst.

The product stream from reactor 201, expected to comprise the cyclic intermediate, e.g., 1,1,2,2-tetrachlorocyclopropane in the case of sodium acetate and vinylidene chloride reactants, as well as unreacted vinylidene chloride and sodium acetate, solvent e.g. chloroform, phase transfer catalyst if used, and trace amounts of the same light and heavy byproducts listed above, is provided to separation unit 203. Separation unit 203 is operated at conditions effective to provide an overhead stream comprising unreacted vinylidene dichloride and solvent, which may be recycled to reactor 201. The bottoms stream from separation unit 203, expected to comprise the cyclic intermediate, unreacted sodium trichloroacetate, sodium chloride, phase transfer catalyst if used, and byproducts is provided to quench unit 205.

Water is fed to quench unit to solubilize the sodium chloride, which is then provided as a waste stream from quench unit 205. The product stream from quench unit, comprising the cyclic intermediate and byproducts is fed to preheater 206, operated at conditions effective to vaporize the lighter organics and allow for the removal of heavier, nonvaporized byproducts as a bottoms stream.

The product stream from heater 206 is fed to reactor 212, and the flow therethrough that may be assisted with an inert carrier gas as may be provided by carrier gas source 210. As in process 100, reactor 212 may be a hot tube reactor, and may be packed, if desired. The product stream therefrom is expected to comprise 1,1,2,3-tetrachloropropene and heavier by products and is provided to separation unit 214.

Separation unit 214 is operated at conditions effective to provide a top stream comprising the (any) cyclic intermediate that may be disposed of as waste, or recycled to reactor 212, and a bottoms stream comprising 1,1,2,3-tetrachloropropene and heavier by products. The bottoms stream from separation unit 214 is provided to separation unit 216, which would then provide a substantially pure stream of 1,1,2,3-tetrachloropropene in an overhead stream and the heavier byproducts out a waste bottoms stream.

Process 200 thus requires fewer separation steps than process 100, due at least to the removal of unreacted vinylidene dichloride via the overhead stream of heater 203 as well as minimal byproducts formed by the neutral aqueous generation of dichlorocarbene in reactor 201.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated and/or fluorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 1-chloro-3,3,3-trifluoropropene (1233zd). Catalytic hydrofluorination of 1,-chloro-3,3,3-trifluoropropene would give 1-chloro-2,3,3,3-tetrafluoropropene. The 1-chloro-2,3,3,3-tetrafluoropropane is then dehydrochlorinated to 1,3,3,3-tetrafluoropropene via a catalyzed, gas phase reaction.

The selectivities reported herein have been calculated by analyzing the outlet stream to quantify the amount of all species present and removing the starting materials. The percent of the cyclic intermediate and all species derived therefrom is then calculated based upon the outlet stream content, minus the starting materials. For example, an outlet stream consisting of 45.58% vinylidene dichloride, 53.54% chloroform, 0.03% 2,3,3,3-tetrachloropropene, 0.51% 1,1,2,2-tetrachlorocyclopropane, 0.09% pentachloroethane, 0.16% 1,1,2,3-tetrachloropropene, 0.08% hexachloroethane, and 0.02% hexachlorobutene was calculated to have a selectivity of 78.3% (0.03%+0.51%+0.09%+0.16%+0.08%+0.02%=0.89%; 0.03/0.89=0.033 (2333); 0.51/0.89=0.57 (1122); 0.09/0.89=0.10 (penta); 0.16/0.89=0.18 (1123); 0.08/0.89=0.09 (hexa); 0.02/0.89=0.02 (hexa) 3.3%+57%+18%=78.3%)

Example #1

A liquid feed of chloroform pumped at a rate of 1.0 milliliters per minute is vaporized and preheated to 300° C. A separate liquid feed of vinylidene chloride pumped at a rate of 0.4 milliliters per minute is vaporized and preheated to 100° C. The two gaseous feeds are mixed under adiabatic conditions and carried through a hot-tube reactor operating at 500° C. and 5 psig by a nitrogen stream flowing at 10 standard cubic centimeters per minute.

The output gas stream is condensed in a collection flask and the resulting liquid is analyzed by gas chromatography coupled with mass spectrometry for identification of the components in the product mixture. The major species in the product mixture are found to be 26.6% 1,1,2,3-tetrachloropropene, 19.4% chloroform, 17.3% vinylidene chloride amongst various other chlorocarbon byproducts. Proton nuclear magnetic resonance spectroscopy confirms the yield of 1,1,2,3-tetrachloropropene to be 67%, accounting for recovered starting material.

Example #2

A liquid feed of chloroform pumped at a rate of 2.0 milliliters per minute is vaporized and preheated to 250° C. A separate liquid feed of vinylidene chloride pumped at a rate of 0.2 milliliters per minute is vaporized and preheated to 50° C. The two gaseous feeds are mixed under adiabatic conditions and carried through a hot-tube reactor operating at 400° C. and 5 psig by a nitrogen stream flowing at 10 standard cubic centimeters per minute.

The output gas stream is condensed in a collection flask and the resulting liquid is analyzed by gas chromatography coupled with mass spectrometry for identification of the components in the product mixture. The product mixture is found to be 99% recovered starting material, 0.55% 1,1,2,2-tetrachlorocyclopropane, 0.18% 1,1,2,3-tetrachloropropene, and a balance of chlorocarbon residues. This example shows that utilization of lower temperatures, and particularly a lower temperature than used in Example #1, provides high selectivity towards the desired tetrachlorocyclopropane and acyclic tetrachloropropene with minimal formation of chloroform thermal degradation byproducts.

Example #3

A liquid feed of chloroform pumped at a rate of 1.0 milliliters per minute is vaporized and preheated to 300° C. A separate liquid feed of vinylidene chloride pumped at a rate of 0.4 milliliters per minute is vaporized and preheated to 100° C. The two gaseous feeds are mixed under adiabatic conditions and carried through a hot-tube reactor operating at 450° C. and 5 psig by a nitrogen stream flowing at 10 standard cubic centimeters per minute.

The output gas stream is condensed in a collection flask and the resulting liquid is analyzed by gas chromatography coupled with mass spectrometry for identification of the components in the product mixture. The product mixture is found to be 84% recovered starting material, 8.1% 1,1,2,3-tetrachloropropene, and 2.4% 1,1,2,2-tetrachlorocyclopropane. This Example provides the best combined yield and selectivity of all Examples, and shows that temperature can provide a sensitive adjustment to the yield of the acyclic tetrachloropropene.

Example #4

A 100 mL round-bottom flask equipped with reflux condenser, magnetic stir bar, and mineral oil bubbler is charged with 0.63 g of tetrabutylammonium chloride, 10 g of sodium trichloroacetate, 25 mL of chloroform, and 12 mL of vinylidene chloride. The reaction mixture is heated to reflux and allowed to stir for 12 hours. After this time, the reaction mixture is cooled to ambient temperature and the organic fraction is collected by decantation. Drying of the organic fraction and removal of excess solvent allows for the recovery of 5.6 g of material that, according to proton nuclear magnetic resonance spectroscopy, contains 12.4% 1,1,2,2-tetrachlorocyclopropane and a large amount of unreacted starting material.

This Example shows that the process can be carried in the liquid phase, and that doing so can allow for removal of unreacted vinylidene dichloride. Removal of excess vinylidene dichloride will, in turn, reduce the number of byproducts produced thereby, and as a consequence, the number of downstream purification steps necessary to recover product from the process.

The invention claimed is:

1. A process for the production of chlorinated propenes, comprising reacting vinylidene chloride with sodium trichloroacetate and/or chloroform, or, reacting perchloroethylene with diazomethane to provide 1,1,2,2,-tetrachlorocyclopropane and converting the 1,1,2,2,-tetrachlorocyclopropane to the desired chlorinated propene.

2. The process of claim 1, wherein the sodium trichloroacetate, chloroform or diazomethane generate a carbene in situ.

3. The process of claim 2, wherein the carbene comprises methylene, dichlorocarbene, or a combination of these.

4. The process of claim 1, comprising reacting chloroform and vinylidene chloride.

5. The process of claim 1, wherein the chloroform is preheated to a temperature of from 250° C. to 400° C.

6. The process of claim 4 wherein the chloroform and vinylidene chloride are passed through a hot tube reactor.

7. The process of claim 6, wherein the chloroform and vinylidene chloride are mixed prior to being heated above 400° C.

8. The process of claim 6, wherein the hot tube reactor is operated at temperatures of from 400° C. to 600° C.

9. The process of claim 6, wherein the hot tube reactor is operated at pressures of from 0-10 psig.

10. The process of claim 6, further comprising passing a carrier gas through the hot tube reactor.

11. The process of claim 2, wherein the 1,1,2,2,-tetrachlorocyclopropane is prepared in the liquid phase from sodium trichloroacetate and vinylidene chloride.

12. The process of claim 1, wherein the chlorinated propene comprises 1,1,2,3-tetrachloropropene.

13. A continuous process for the production of chlorinated propenes, comprising passing vinylidene chloride and chloroform through a hot tube reactor to provide 1,1,2,2,-tetrachlorocyclopropane and converting the 1,1,2,2,-tetrachlorocyclopropane to the desired chlorinated propene, wherein the cyclopropane is prepared from reactants comprising chloroform and vinylidene chloride which are passed through a hot tube reactor.

* * * * *